(12) United States Patent
Perkins et al.

(10) Patent No.: US 9,955,915 B2
(45) Date of Patent: May 1, 2018

(54) BALL JOINT CENTER LOCATING METHOD USING DATA FROM ATTACHED INERTIAL MEASUREMENT UNIT

(71) Applicant: THE REGENTS OF THE UNIVERSITY OF MICHIGAN, Ann Arbor, MI (US)

(72) Inventors: Noel Perkins, Ann Arbor, MI (US); Ryan McGinnis, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 476 days.

(21) Appl. No.: 14/423,852

(22) PCT Filed: Aug. 29, 2013

(86) PCT No.: PCT/US2013/057303
§ 371 (c)(1),
(2) Date: Feb. 25, 2015

(87) PCT Pub. No.: WO2014/036269
PCT Pub. Date: Mar. 6, 2014

(65) Prior Publication Data
US 2015/0223753 A1 Aug. 13, 2015

Related U.S. Application Data

(60) Provisional application No. 61/694,790, filed on Aug. 30, 2012.

(51) Int. Cl.
*G01B 7/00* (2006.01)
*A61B 5/00* (2006.01)
(Continued)

(52) U.S. Cl.
CPC ............ *A61B 5/4851* (2013.01); *A61B 5/076* (2013.01); *A61B 5/1112* (2013.01);
(Continued)

(58) Field of Classification Search
CPC ............ A61B 2562/0219; A61B 17/56; A61B 17/1764; A61B 5/1112
(Continued)

(56) References Cited

U.S. PATENT DOCUMENTS 6,923,817 B2    8/2005  Carson et al.
8,118,815 B2    2/2012  van der Walt
(Continued)

FOREIGN PATENT DOCUMENTS

EP    2181740 A2    5/2010

OTHER PUBLICATIONS

Schwartz, Michael H. et al., "A New Method for Estimating Joint Parameters From Motion Data," Journal of Biomechanics, vol. 38, (2005), pp. 107-116.
(Continued)

*Primary Examiner* — An Do
(74) *Attorney, Agent, or Firm* — Harness, Dickey & Pierce, P.L.C.

(57) ABSTRACT

A method for calculating the location of the center-of-rotation of a joint with an attached member. The method employs an inertial measurement unit (IMU) having an angular rate gyro and an accelerometer and coupling the inertial measurement unit to the member for detection of movement of the member. The inertial measurement unit outputs data representative of angular velocity and acceleration of the member mounted IMU in response to movement of the joint. The method further comprising analyzing the angular rate and acceleration data to determine the center-of-rotation of the joint.

19 Claims, 3 Drawing Sheets

(51) Int. Cl.

| | |
|---|---|
| G01B 21/04 | (2006.01) |
| G01M 13/04 | (2006.01) |
| G01S 19/49 | (2010.01) |
| A61B 5/11 | (2006.01) |
| A61F 2/46 | (2006.01) |
| A61F 5/01 | (2006.01) |
| A61B 5/07 | (2006.01) |
| A61F 2/30 | (2006.01) |

(52) U.S. Cl.
CPC ............ *A61B 5/1121* (2013.01); *A61B 5/686* (2013.01); *A61B 5/742* (2013.01); *A61F 2/30* (2013.01); *A61F 2/4657* (2013.01); *A61F 5/0113* (2013.01); *G01B 21/04* (2013.01); *G01M 13/04* (2013.01); *G01S 19/49* (2013.01); *A61B 2562/0219* (2013.01); *A61B 2562/0223* (2013.01); *A61F 2250/0002* (2013.01)

(58) Field of Classification Search
USPC ............... 702/127, 141, 142, 145, 151, 155; 600/302, 595
See application file for complete search history.

(56) References Cited

U.S. PATENT DOCUMENTS

| | | | | |
|---|---|---|---|---|
| 8,944,939 | B2* | 2/2015 | Clark | ................ G01P 13/00 463/36 |
| 9,649,160 | B2* | 5/2017 | van der Walt | ......... A61B 34/20 |
| 2002/0008661 | A1 | 1/2002 | McCall et al. | |
| 2003/0024311 | A1 | 2/2003 | Perkins | |
| 2010/0103095 | A1 | 4/2010 | Yamamoto et al. | |
| 2011/0218543 | A1 | 9/2011 | van der Walt | |

OTHER PUBLICATIONS

Kurtz, Steven, et al. "Projections of Primary and Revision Hip and Knee Arthroplasty in the United States from 2005 to 2030," The Journal of Bone & Joint Surgery, vol. 89A, No. 4, pp. 780-785 (Apr. 2007).

Kinzl, L., et al. "Total Knee Arthroplasty—Navigation as the Standard," Chirurg, vol. 75, No. 10, pp. 976-981 (Oct. 2004). English Abstract.

King, Kevin, et al. "Bowling Ball Dynamics Revealed by Miniature Wireless MEMS Inertial Measurement Unit," Sports Engineering, vol. 13, No. 2, pp. 95-104 (Oct. 2010).

Siston, Robert A., et al. "Evaluation of a New Algorithm to Determine the Hip Joint Center," Journal of Biomechanics, vol. 39, pp. 125-130 (2006).

Ehrig, Rainald M., et al. "The SCoRE Residual: A Quality Index to Assess the Accuracy of Joint Estimations," Journal of Biomechanics, vol. 44, pp. 1400-1404 (2011).

Schmidt-Wetekam, Christopher, et al. "Inertial Rotation Center Position Estimation for a Perching Treaded Vehicle," IEEE/RSJ International Conference on Intelligent Robots and Systems, pp. 4097-4102 (Sep. 25-30, 2011) San Francisco, CA.

Simo, J.C., et al. "Non-Linear Dynamics of Three-Dimensional Rods: Exact Energy and Momentum Conserving Algorithms," International Journal for Numerical Methods in Engineering, vol. 38, pp. 1431-1473 (1995).

MacWilliams, Bruce A., "A Comparison of Four Functional Methods to Determine Centers and Axes of Rotations," Gait Posture (2008).

Favre, J., et al. "Ambulatory Measurement of 3D Knee Joint Angle," Journal of Biomechanics, vol. 41, pp. 1029-1035 (2008).

McGinnis, Ryan, et al. "Reconstructing Free-Flight Angular Velocity from a Miniaturized Wireless Accelerometer," Journal of Applied Mechanics, vol. 79 (Jul. 2012).

King, Kevin W.: "The Design and Application of Wireless MEMS Inertial Measurement Units for the Measurement and Analysis of Golf Swings", Ph.D. dissertation, University of Michigan, 2008, Ann Arbor, MI.

International Search Report and Written Opinion (both in English) for PCT/US2013/057303, dated Dec. 5, 2013; ISA/KR.

* cited by examiner

BALL JOINT CENTER LOCATING METHOD USING DATA FROM ATTACHED INERTIAL MEASUREMENT UNIT

CROSS-REFERENCE TO RELATED APPLICATIONS

This application claims the benefit of U.S. Provisional Application No. 61/694,790, filed on Aug. 30, 2012. The entire disclosure of the above application is incorporated herein by reference.

FIELD

The present disclosure relates to a method for calculating the location of a ball joint and, more particularly, relates to a method for calculating the location of a ball joint (or other joint) using data from one or more inertial measurement units.

BACKGROUND AND SUMMARY

This section provides background information related to the present disclosure which is not necessarily prior art. This section provides a general summary of the disclosure, and is not a comprehensive disclosure of its full scope or all of its features.

The present teachings provide a new method for calculating the location of the center-of-rotation of a ball joint (or other joint) using data from an inertial measurement unit. This method has applications specific to joint replacement surgeries, to joint injury prevention and treatment, and also to the science and practice of biomechanics.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
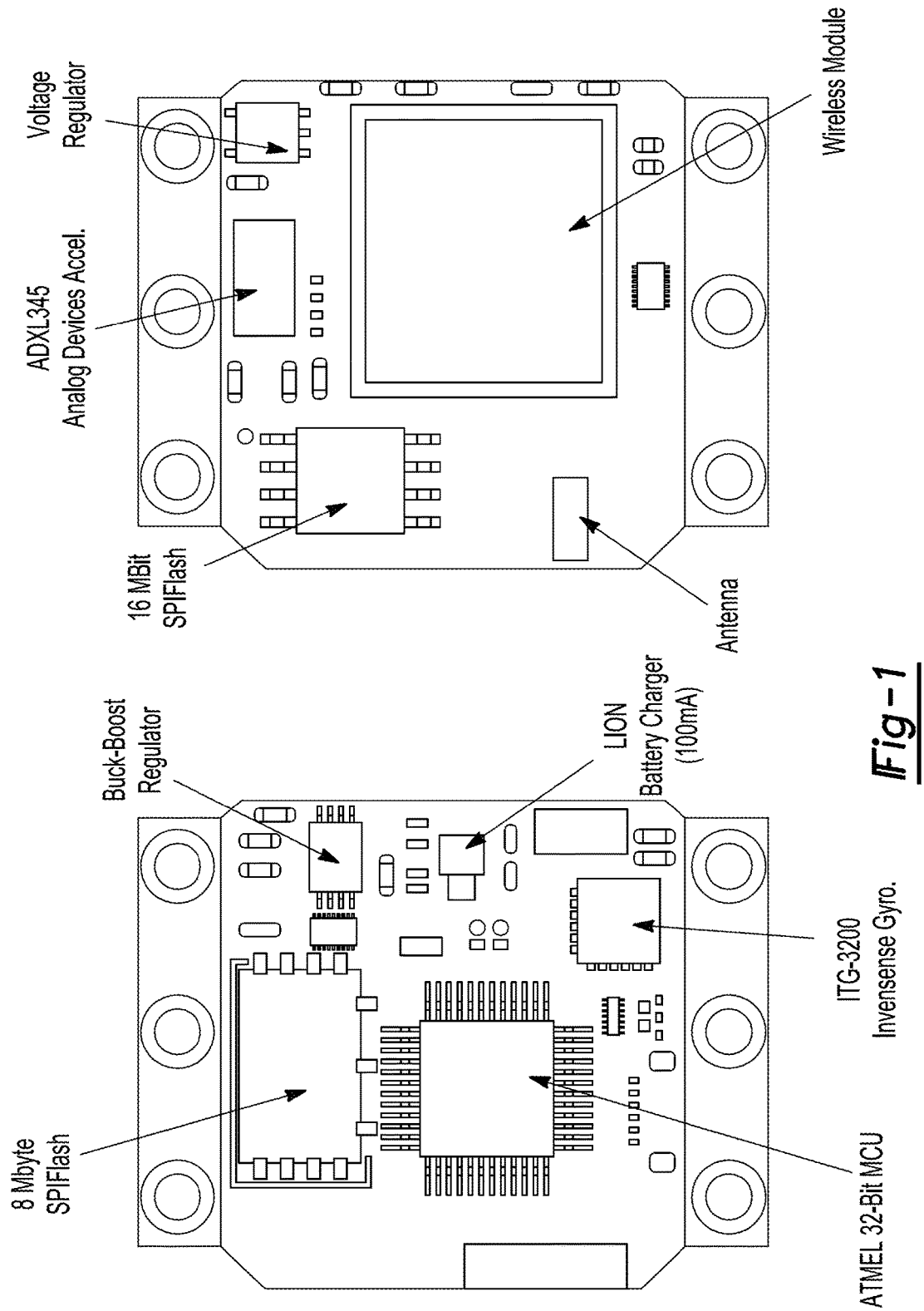
FIG. 1 is a series of photographs of an inertial measurement unit according to the principles of the present teachings.

Example embodiments will now be described more fully with reference to the accompanying drawings.

Example embodiments are provided so that this disclosure will be thorough, and will fully convey the scope to those who are skilled in the art.

Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The number of total hip and knee replacement surgeries performed every year is predicted to increase by 174% (to 572,000) and 673% (to 3.48 million) respectively by 2030. An important contributor to the success of both hip and knee replacement surgeries is accurate identification of the center-of-rotation (CoR) of the hip. Moreover, it is important to develop methods for the early assessment and treatment of these joint injuries to help curb these alarming trends.

According to the principles of the present teachings, in some embodiments, inverse dynamic analysis combines kinematic and physical information about the body segments on either side of a joint with the location of the center-of-rotation to determine joint loading. Integral to this analysis is accurate estimation of the location of the joint center. To date, methods for deducing the center-of-rotation of joints fall into two categories: anatomical and functional. Anatomical techniques rely on imaging or palpation to define the location of bony landmarks, from which anthropometric data provide an estimate of the joint center-of-rotation. Functional methods rely on video-based motion capture to track the 3-D position of a set of reflective markers attached to the body segments on either side of the joint during some prescribed motion. The path of the markers allows for an estimate of the joint's center-of-rotation. The present method uses data from an inertial measurement unit (IMU) to estimate the position of center-of-rotation of the hip.

The present teachings disclose a new method for calculating the location of the center-of-rotation of a ball joint or other joint (such as a hinged joint) using data from an inertial measurement unit (IMU). As emphasized herein, this method has applications specific to joint replacement surgeries, to joint injury prevention and treatment and also to the science and practice of biomechanics. Herein, the IMU technology used to demonstrate the success of the present method is described. Following this, an algorithm for accurately estimating joint center-of-rotation location is presented. The results of a benchmarking study which demonstrate the accuracy of the present teachings are also presented.

Description of the Supporting IMU Technology and the Collection of IMU Data

In some embodiments, the present method employs an IMU to obtain kinematic data. FIG. 1 illustrates the wireless IMU used in this study.

In some embodiments, the IMU is equipped with a low-power Wi-Fi module, or other wireless communication module, such as a Bluetooth module, which enables data collection over a standard Wi-Fi network (or Bluetooth communication system) by a computer. The design includes a digital tri-axial angular rate gyro and accelerometer, which can, in some embodiments, perform internal 16-bit and 13-bit A/D conversion with measurement ranges of 2000 deg/s and 16 g, and sampling frequencies of 512 and 800 Hz respectively. Data can be logged in 8 Mbytes of onboard flash memory during each trial and can be downloaded to the host computer or processor upon the trial's completion. Before its first use, the IMU is calibrated according to the procedure detailed in K. W. King, "The design and application of wireless MEMS inertial measure units for the measurement and analysis of golf swings," Ph.D. dissertation, University of Michigan, Ann Arbor, Mich. 2008. The calibration routine is composed of a set of rotations about each of three orthogonal axes, and is used to determine 24 calibration parameters (including scale factors, cross-axis sensitivity scale factors, and biases) for the IMU. This process ensures that the acceleration and angular rate measurements are accurate and resolved along a common orthogonal triad of unit vectors. Additionally, bias values for the angular rate gyro are updated at the start of every trial to ensure that any alteration in bias due to environmental variations is accounted for.

Figure 2A:
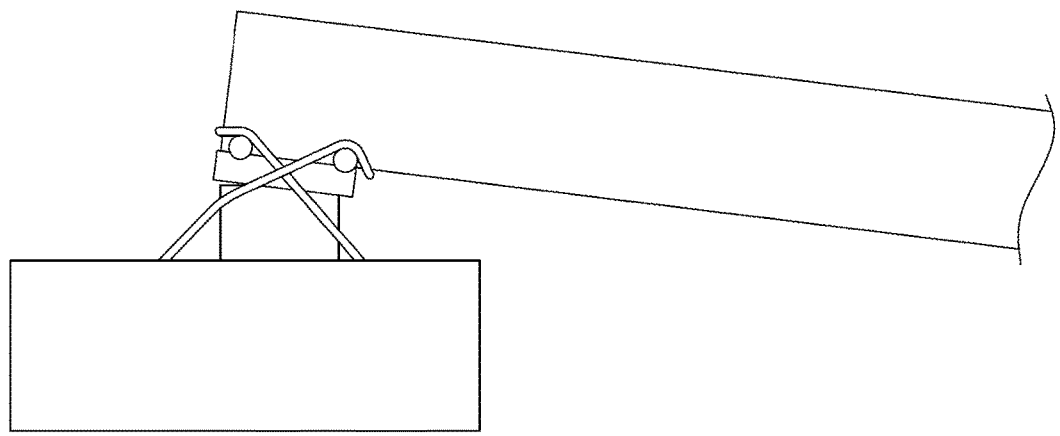
FIG. 2 is a series of photographs of a mechanical approximation of a human ball joint.
Figure 2B:
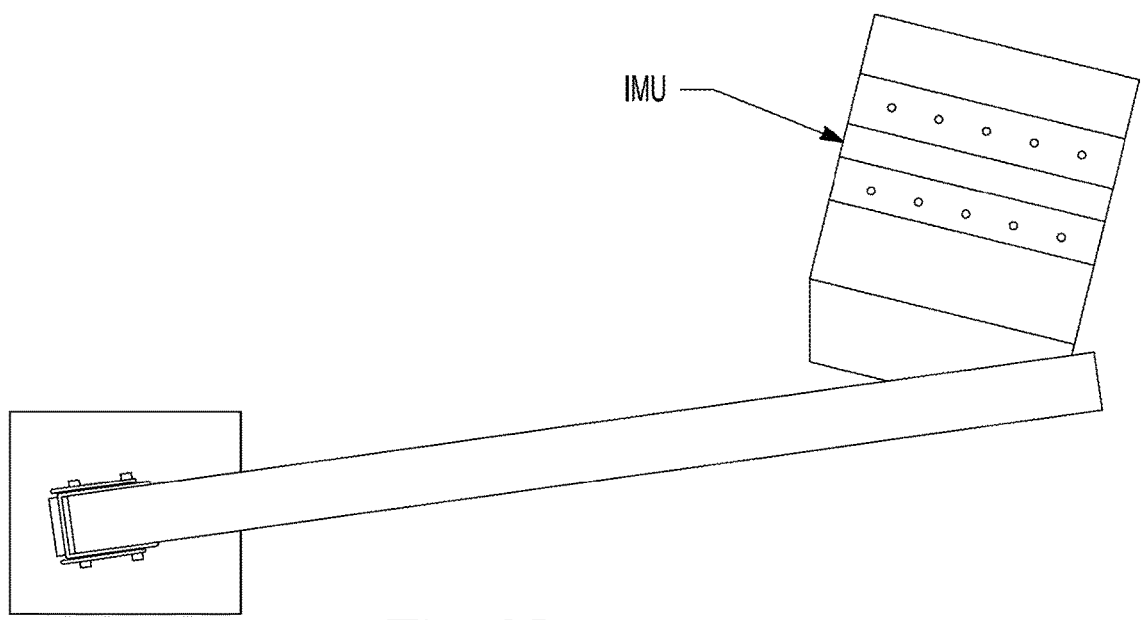

The experimental apparatus presented in FIG. 2 is a mechanical approximation of a human ball joint (FIG. 2A) and the appendage which forms the distal side of that joint (FIG. 2B). What would constitute the proximal side of the joint is fixed to a rigid support while the distal side, including the IMU as noted in FIG. 2B, is left free to be manipulated. The joint itself is held together with two rubber O-rings as shown in FIG. 2A.

It should be appreciated, for example, that the ball joint shown in FIG. 2A is a model of a typical human hip joint, where the proximal (black) and distal (white and ball bearing) sides of the joint correspond to the acetabular cup and femoral stem/head respectively. The purpose of using the mechanical analog is to demonstrate the accuracy of the present method.

The present method relies on IMU data collected during two motions; namely a circumduction (Cir) motion and a rotation (Rot) about the long axis of the femur. (Either motion or different motions may also provide the data needed to estimate the joint location.) Following each of these motions, the femur is again at rest. IMU data from a representative trial approximately 60 seconds in length is presented in FIG. 3. (Trials of shorter or longer lengths may also provide the data needed to estimate the joint location.) The data collected can be stored in on-board flash memory, non-transitory memory, and/or immediately transferred (via wired or wireless connection) to a data storage device and/or processor.

Figure 3B:
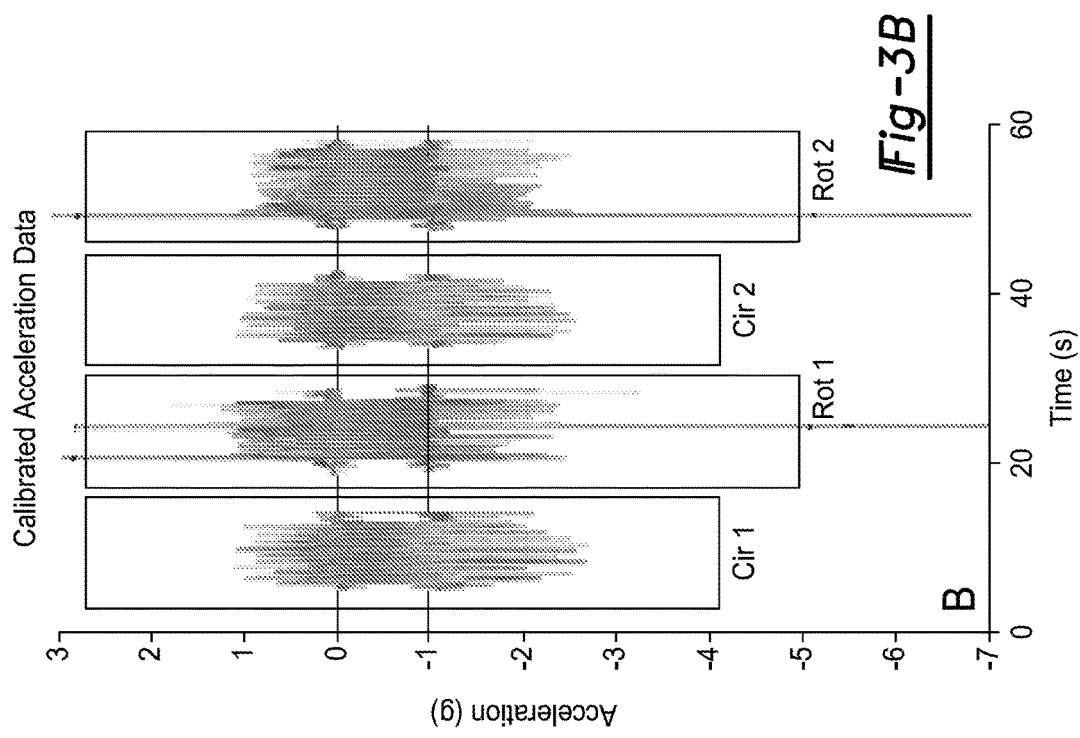
FIG. 3B is a graph illustrating calibrated acceleration data from an inertial measurement unit.
Figure 3A:
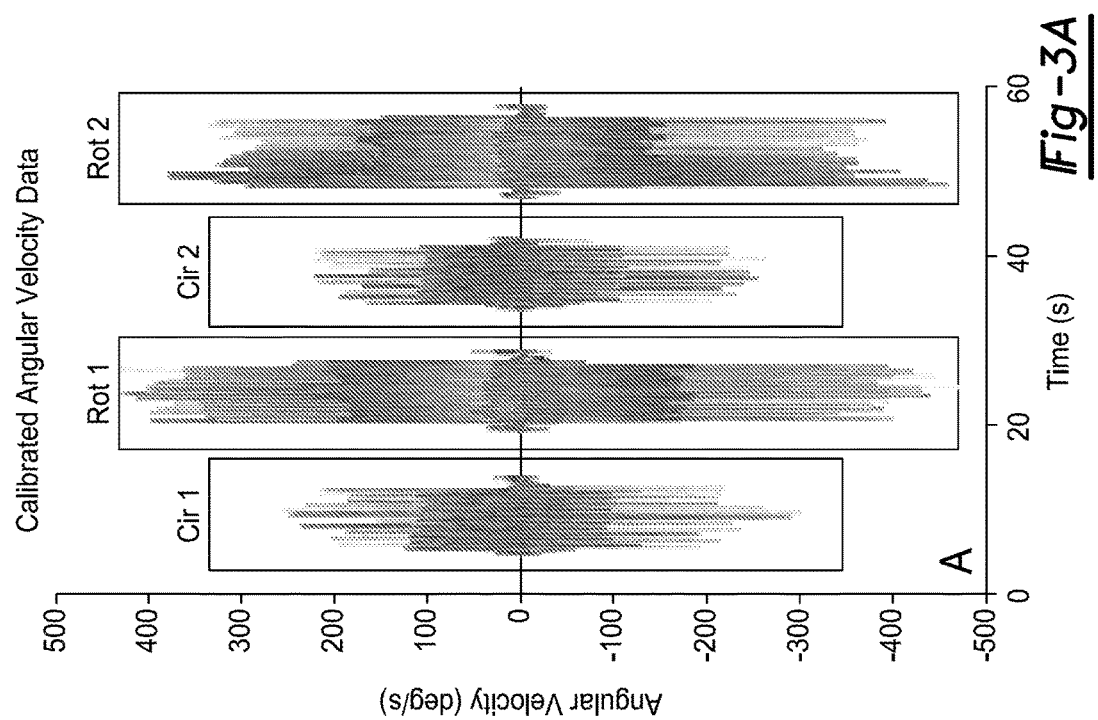
FIG. 3A is a graph illustrating calibrated angular velocity data from an inertial measurement unit.

FIG. 3A and FIG. 3B show the calibrated angular velocity and acceleration data for a typical trial respectively. The circumduction motions are highlighted by boxes with "Cir" annotations while the rotation motions are highlighted by boxes with "Rot" annotations. Between these motions, the artificial femur is at rest; note the angular velocity is zero during these phases and the acceleration achieves a value of 1 g.

To remove gravity from the measured acceleration value, it is helpful to introduce two frames of reference: an "IMU-fixed" frame denoted by the mutually orthogonal triad of unit vectors ($\hat{x}$, $\hat{y}$, $\hat{z}$,) and an inertial, "lab-fixed" frame denoted by the mutually orthogonal triad of unit vectors ($\hat{X}$, $\hat{Y}$, $\hat{Z}$). The measured IMU quantities are reported in this IMU-fixed reference frame, while the measured value of gravity is defined to be +1 g in the $\hat{Z}$ direction. The lab-fixed $\hat{X}$ and $\hat{Y}$ are determined by the initial orientation of the IMU. The transformation that relates these two frames, which we will refer to as the direction cosine matrix (DCM), is then defined in eq. (1).

$$\vec{x}|_{\hat{X}, \hat{Y}, \hat{Z}} = \Lambda \vec{x}|_{\hat{x}, \hat{y}, \hat{z}} \quad (1)$$

Where $\Lambda$ is the direction cosine matrix, $\vec{x}|_{\hat{X}, \hat{Y}, \hat{Z}}$ are the components of a vector $\vec{x}$ resolved in the IMU-fixed frame, and $\vec{x}|_{\hat{x}, \hat{y}, \hat{z}}$ are the components of the same vector $\vec{x}$ resolved in the lab-fixed frame. As defined, the IMU-fixed frame is translating and rotating with respect to the lab fixed frame. The method for constructing the DCM as a function of time is based on a numerical solution to the differential equation governing the evolution of the DCM as shown in eq. (2).

$$\dot{\Lambda} = \Lambda \vec{\omega}^{\times} \quad (2)$$

Where $\dot{\Lambda}$ is the time derivative of the DCM and $\vec{\omega}^{\times}$ is the IMU-fixed angular velocity in skew-symmetric form. The midpoint solution method can be rearranged to solve for the DCM at time step n+1 in terms of the DCM at time step n, and the IMU-fixed angular velocity vector at time steps n and n+1. This explicit relationship is shown in eq. (3).

$$\Lambda_{n+1} = \Lambda_n \left[I + \frac{1}{2}\vec{\theta}^x\right]\left[I - \frac{1}{2}\vec{\theta}^x\right]^{-1} \quad (3)$$

where $\vec{\theta}^x$ is the midpoint approximation of the change in orientation from time step n to step n+1 as defined in eq. (4), in skew-symmetric form.

$$\vec{\theta} = \frac{1}{2}\Delta t(\vec{\omega}_{n+1} + \vec{\omega}_n) \quad (4)$$

where $\vec{\omega}_{n-1}$ and $\vec{\omega}_n$ are the IMU-fixed angular velocities at time steps n+1 and n respectively, and Δt is the change in time between time steps n and n+1. The IMU gives the IMU-fixed angular velocity needed to solve eq. (3) starting from an initial value for the DCM ($\Lambda_0$). This initial value is determined by assessing the measured acceleration of the IMU while at rest at the start of each trial. With this information, one can then solve for the DCM as a function of time $\Lambda(t)$. With the orientation of the IMU relative to the lab-fixed frame determined as a function of time, one can solve for the acceleration of the center of the accelerometer at any instant in time according to eq. (5).

$$\vec{a}_a = \Lambda^T[\Lambda \cdot \vec{a}_m - 1\mathscr{G}\hat{Z}] \quad (5)$$

Where $\vec{a}_a$ is the acceleration of the center of the accelerometer in the IMU-fixed frame of reference, and $\vec{a}_m$ is the measured acceleration. This calculation is needed as input to the new method for joint center calculation described next.

New Method for Estimating Position of Joint center-of-rotation

We begin by considering the kinematic relationship between the acceleration of the center of the mechanical joint we have constructed and the acceleration of the center of the accelerometer mounted on the femur. This relationship is expressed as eq. (6).

$$\vec{a}_a = \vec{a}_c + \dot{\vec{\omega}} \times \vec{r}_{a/c} + \vec{\omega} \times (\vec{\omega} \times \vec{r}_{a/c}) \quad (6)$$

$$\vec{\varepsilon} = \begin{bmatrix} \vec{a}_{a_1} \\ \vdots \\ \vec{a}_{a_n} \end{bmatrix} - \begin{bmatrix} \dot{\vec{\omega}}_1^x + \vec{\omega}_1^x \vec{\omega}_1^x \\ \vdots \\ \dot{\vec{\omega}}_n^x + \vec{\omega}_n^x \vec{\omega}_n^x \end{bmatrix} \vec{r}_{a/c} \quad (7)$$

Where $\vec{a}_a$ is the measured acceleration of the center of the accelerometer, $\vec{a}_c$ is the acceleration of the joint center, $\vec{\omega}$ is the measured angular velocity of the femur, $\dot{\vec{\omega}}$ is the angular acceleration (known by numerical differentiation of the measured angular velocity), the superscript x denotes a vector in skew-symmetric form, and $\vec{r}_{a/c}$ is the unknown position of the accelerometer relative to the center of the ball joint. It is the quantity $\vec{r}_{a/c}$ that we need to compute to locate the joint center. If one assumes that the ball joint forms the pivot of a spherical pendulum, then $\vec{a}_c = 0$ and eq. (6) is linear in the only unknown, and $\vec{r}_{a/c}$ can be solved for directly. Moreover, if one writes eq. (6) for each of n samples of IMU data and writes the equations in the form of an error, as shown in eq. (7), then a solution for $\vec{r}_{a/c}$ which minimizes the squared error can be found.

The ball joint considered in this experiment, like those of the actual human body, has some compliance. As a result, our assumption that the femur behaves like a spherical pendulum is true for some parts of a trial, but not for others. Therefore, it is possible to assess the degree to which each IMU sample conforms to the spherical pendulum assumption by examining the tangential component of the acceleration. The tangential acceleration and an equation which assesses the degree to which the spherical pendulum assumption is met are defined in eqs. (8) and (9) respectively.

$$\vec{a}_t = \vec{a}_a - \left(\frac{\vec{a}_a \cdot \vec{r}}{\|\vec{r}\|^2}\right)\vec{r} \quad (8)$$

$$\vec{\varepsilon}_t = \vec{a}_t - \dot{\vec{\omega}} \times \vec{r} \quad (9)$$

Where $\vec{a}_t$ is the tangential acceleration and $\vec{r}$ is the position of the accelerometer relative to the location of the joint center determined by solving eq. (6) with a given sample of IMU data. For the best results when compared to the benchmark described next, we found that one should analyze approximately 80% of the IMU samples with the smallest sum squared error in the spherical pendulum assumption (i.e. $\vec{\varepsilon}_t^T \vec{\varepsilon}_t \approx 0$). This provides enough data for a robust least squares solution to eq. (7) while neglecting data where the spherical pendulum assumption is clearly not met.

The final determination or calculation of the center-of-rotation location can then be displayed to a user, such as via a monitor, printout, illustration, or other display means, to permit conceptualization of the actual center-of-rotation of the joint. This location can also be used for the treatment of a patient (e.g. joint replacement and the like) and/or used for other non-treatment purposes, such as sports training, conditioning, technique analysis, apparel or equipment design, and the like.

Evidence Supporting the Accuracy of this Method

To demonstrate the accuracy of this method for determining the location of the center of ball joints using IMU data, we present a benchmark experiment comparing the results from 14 distinct 60-second trials against the results from 14 trials collected using a MicroScribe G2X Digital Coordinate Measuring Machine (CMM). This machine, which has positional accuracy (resolution) of 0.23 mm (0.13 mm), is used to digitize the location of the center of the accelerometer, as well as a number of points on the surface of the ball bearing that defines the center-of-rotation of our mechanical joint. Points on the IMU fixture are also digitized to define the direction cosine matrix which describes the orientation of the IMU-fixed reference frame relative to the measurement frame of the CMM machine. The collection of 3-D positions recorded by the CMM machine are used as the input for a custom Matlab™ program which calculates the position of the center of the ball joint relative to the center of the accelerometer in the IMU-fixed reference frame.

Table 1 summarizes the results from the benchmarking experiment. The average (and standard deviation) for each of the three components of the position vector locating the center of the ball joint relative to the center of the accelerometer in the IMU-fixed reference frame are reported.

TABLE 1

Summary of benchmarking experiment, mean (standard deviation) of each component of the joint center position for 14 trials of CMM and IMU data in mm.

| Method | x (mm) | y (mm) | z (mm) |
|---|---|---|---|
| CMM | −342.53 (0.37) | 288.92 (0.38) | 27.90 (0.21) |
| IMU | −340.06 (4.97) | 291.56 (2.97) | 29.56 (1.52) |

It is apparent from these results that the IMU based method of the present teachings for identifying the position of the ball joint center relative to the accelerometer is remarkably accurate. Note that the average errors between the CMM (truth data) and IMU data are 2.47, 2.63, and 1.65 mm in the x, y, and z directions respectively (vector magnitude of 3.97 mm). Thus the IMU method resolves the position of the joint center within approximately 2 mm in any of the three Cartesian directions. This error is comparable to the results of other popular methods that employ video-based techniques for determining joint center locations which are shown to have errors ranging from 1-6 mm on average for a set of 36 trials. However, video-based motion capture methods are substantially more cumbersome and time consuming to use (e.g., they could not realistically be used in the OR). They are also substantially more expensive yet not more accurate than the method above using an IMU.

Existing Technologies

To the best of our knowledge, there is only one inertial sensor based method for deducing the location of the center-of-rotation of a ball joint.

This method is disclosed in U.S. Pat. No. 8,118,815 entitled "Systems and Methods For Joint Replacement", which makes use of inertial sensors to aid surgeons in knee replacement surgeries. This patent appears to disclose a method for finding the location of the center of the hip joint, a step that is necessary to properly locate the components of a prosthetic knee, by first computing the velocity and position of the IMU (as calculated from IMU data). They then utilize commonly known kinematic relationships to deduce the location of the center of the hip joint from this data. However, using an IMU to deduce velocity and position, as disclosed in the '815 patent, is highly susceptible to error, particularly drift error. This drift error is introduced by the need to integrate the acceleration data. By contrast, the method that forms the basis of this present disclosure, while sharing the same goal as the '815 patent, utilizes the acceleration and angular velocity directly measured by the IMU, to estimate the center-of-rotation of any ball joint without ever computing the velocity and position. Thus, the present method entirely avoids using error-prone estimates of velocity and position (i.e., avoids any need to integrate the acceleration data) in arriving at the joint center location. Based on this assessment, the method presented above is 1) distinct from that disclosed in the '815 patent and, 2) should provide superior results for locating the center-of-rotation of a ball joint.

Beyond the IMU-based approach, other methods have been presented for joint center locating which use multiple video cameras to track the position of reflective markers attached to each side of the joint as also discussed above. However, these methods require the use of expensive camera systems, specific lighting conditions, and an operator skilled in the collection and analysis of the resulting motion data. In joint replacement surgeries specifically, robots are sometimes used to assist surgeons in placing and orienting the various components of the prosthetic joint. However, these robots are expensive and actually increase the duration of surgeries. Additionally, the methods for joint center location used by these robots are too invasive to be used in any other context (e.g. outside the OR).

Possible Modifications

One possible modification to the method described herein is its extension to the other joints of the human body. Namely, one can identify the location of the axis of rotation of "hinge" joints like the elbow and knee using data from IMUs and methods similar to those presented here.

Additionally, it should be understood that the inertial measurement unit of the present teachings can further be supplemented with additional sensor components, such as magnetometers, GPS sensors, and the like to provide additional motion data for analysis.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for calculating the location of the center-of-rotation of a joint of a member, said method comprising:
    providing an inertial measurement unit having an angular rate gyro and an accelerometer;
    fixedly coupling said inertial measurement unit to the member for movement therewith;
    outputting data from said inertial measurement unit in response to movement about the joint, said data being representative of angular velocity and acceleration of the member;
    calculating a center-of-rotation location of the joint based directly on said angular velocity data and said acceleration data without need to integrate said acceleration data; and
    outputting said center-of-rotation location.

2. The method according to claim 1 wherein said outputting data from said inertial measurement unit in response to movement about the joint comprises outputting data from said inertial measurement unit in response to movement about the joint via a wireless module.

3. The method according to claim 2 wherein said wireless module is a Wi-Fi module.

4. The method according to claim 2 wherein said wireless module is a Bluetooth module.

5. The method according to claim 1 wherein said outputting data from said inertial measurement unit in response to movement about the joint comprises outputting data from said inertial measurement unit in response to movement about the joint via a wired module.

6. The method according to claim 1 wherein said providing an inertial measurement unit comprises providing an inertial measurement unit having a digital tri-axial angular rate gyro and accelerometer.

7. The method according to claim 1 wherein said providing an inertial measurement unit comprises providing an inertial measurement unit and a magnetometer.

8. The method according to claim 1 wherein said providing an inertial measurement unit comprises providing an inertial measurement unit and a global positioning system (GPS) sensor.

9. The method according to claim 1 wherein said outputting data from said inertial measurement unit in response to movement about the joint comprises outputting data from said inertial measurement unit to a memory device in response to movement about the joint.

10. The method according to claim 1, further comprising:
calibrating said inertial measurement unit prior to said outputting data from said inertial measurement unit in response to movement about the joint.

11. The method according to claim 1 wherein said calculating a center-of-rotation location of the joint based directly on said angular velocity data and said acceleration data comprises calculating a center-of-rotation location of the joint based directly on said angular velocity data and said acceleration data and an associated biasing value, said associated biasing value being predetermined to accommodate environmental variations.

12. A method for computing the location of the center-of-rotation of a joint of a member, said method comprising:
fixedly coupling an inertial measurement unit having an angular rate gyro and an accelerometer to the member for movement therewith;
outputting data from said inertial measurement unit representative of angular velocity and acceleration of the member in response to movement about the joint;
computing a center-of-rotation location of the joint based directly on said angular velocity data and said acceleration data without need to integrate said acceleration data; and
outputting said center-of-rotation location.

13. The method according to claim 12 wherein said outputting data from said inertial measurement unit comprises outputting data from said inertial measurement unit via a wireless module.

14. The method according to claim 13 wherein said wireless module is a Wi-Fi module.

15. The method according to claim 12 wherein said fixedly coupling an inertial measurement unit having an angular rate gyro and an accelerometer to the member for movement therewith comprises fixedly coupling an inertial measurement unit having a digital tri-axial angular rate gyro and accelerometer.

16. The method according to claim 12 wherein said outputting data from said inertial measurement unit representative of angular velocity and acceleration of the member in response to movement about the joint comprises outputting data from said inertial measurement unit representative of angular velocity and acceleration of the member to a flash memory device operably coupled to said inertial measurement unit in response to movement about the joint.

17. The method according to claim 12, further comprising:
calibrating said inertial measurement unit prior to said outputting data from said inertial measurement unit representative of angular velocity and acceleration of the member in response to movement about the joint.

18. The method according to claim 12 wherein said computing a center-of-rotation location of the joint based directly on said angular velocity data and said acceleration data without need to integrate said acceleration data comprises computing a center-of-rotation location of the joint based directly on said angular velocity data and said acceleration data and an associated biasing value, said associated biasing value being predetermined to negate environmental variations.

19. A method for displaying the location of the center-of-rotation of a joint of a limb, said method comprising:
fixedly coupling an inertial measurement unit having an angular rate gyro and an accelerometer to the limb for movement therewith;
outputting data from said inertial measurement unit representative of angular velocity and acceleration of the limb in response to movement about the joint;
computing a center-of-rotation location of the joint based directly on said angular velocity data and said acceleration data via a processor according to a predetermined algorithm without need to integrate said acceleration data, said predetermined algorithm being stored in said processor on a non-transitory media; and
outputting said center-of-rotation location via a display device.

* * * * *